United States Patent
Kraemer et al.

(10) Patent No.: US 9,006,261 B2
(45) Date of Patent: Apr. 14, 2015

(54) FLUORESCENT PERYLENE DERIVATIVES FOR DIRECT DETECTION OF HEPARIN

(76) Inventors: Roland Kraemer, Heidelberg (DE); Helga Szelke, Aarau (CH); Job Harenberg, Heidelberg (DE); Armin Poeck, Heidelberg (DE)

( * ) Notice: Subject to any disclaimer, the term of this patent is extended or adjusted under 35 U.S.C. 154(b) by 539 days.

(21) Appl. No.: 13/390,799

(22) PCT Filed: Aug. 19, 2010

(86) PCT No.: PCT/EP2010/062118
§ 371 (c)(1),
(2), (4) Date: May 7, 2012

(87) PCT Pub. No.: WO2011/020887
PCT Pub. Date: Feb. 24, 2011

(65) Prior Publication Data
US 2012/0220617 A1    Aug. 30, 2012

(30) Foreign Application Priority Data

Aug. 20, 2009   (EP) .................................. 09168292

(51) Int. Cl.
*A61K 31/44* (2006.01)
*C09B 5/62* (2006.01)

(52) U.S. Cl.
CPC ........................ *C09B 5/62* (2013.01)

(58) Field of Classification Search
USPC .......................................................... 514/279
See application file for complete search history.

(56) References Cited

U.S. PATENT DOCUMENTS 5,811,307 A    9/1998  Rill et al.

2002/0012947 A1   1/2002  Bevers
2007/0004919 A1   1/2007  Kohl

OTHER PUBLICATIONS

Despotis et al., 'Anticoagulation Monitoring during Cardiac Surgery', Anesthesiology, 1999, 91, 1122-51.
Franceschin et al., 'The number and distances of positive charges of polyamine side chains in a series of peylene diimides significantly influcende their ability to induce G-quadruplex structrues and inhibit human telomerase', Bioorganic & Medicinial Chemistry, 2008, 16, 2292-2304.
Mecca et al., 'Polycationic calix [8] arenes able to recognize and neutralize heparin', Organic & Biomolecular Chemistry, 2006, 4, 3763-3768.
Sauceda et al., 'Designing Fluorescent Sensors of Heparin', ChemBioChem, 2007, 8, 391-394.
Wang, et al., 'Discovery of heparin chemosensors through diversity oriented flourescence library approach' Chem. Commun. , 2008, 10, 1173-1175.
Wright et al., ' A Functional Assay for Heparin in Serum Using a Designed Synthetic Receptor', Angewandte Chemie International Edition, 2005, 44, 5679.
International Search Report and Written Opinion received in PCT/EP2010/062118, mailed Nov. 8, 2010.

*Primary Examiner* — San-Ming Hui
(74) *Attorney, Agent, or Firm* — Suzannah K. Sundby, Esq.; Canady + Lortz LLP

(57) ABSTRACT

The invention relates to a perylene diimide derivative and to an in vitro method for preparing the same. In addition, the invention relates to a method for detecting heparin in a sample using perylene diimide derivatives, wherein the interaction of the perylene diimide derivative with heparin modulates the intensity of the fluorescent signal of the mixture compared to the solution. The invention also comprises a diagnostic kit for detecting heparin in a sample in vitro, comprising the perylene diimide derivative, as well as the use of the perylene diimide derivative for neutralizing the anticoagulant activity of heparin.

16 Claims, 10 Drawing Sheets

FLUORESCENT PERYLENE DERIVATIVES FOR DIRECT DETECTION OF HEPARIN

This application is a 371 National Phase entry of PCT/EP2010/062118 filed 19 Aug. 2010, and claims the benefit of European Patent Application Serial No. 09168292.2, filed 20 Aug. 2009, both of which are herein incorporated by reference in their entirety.

FIELD OF THE INVENTION

The present invention relates to perylene diimide derivatives of formulae I, II and III, and to a method for preparing the same. The invention also relates to an in vitro method for detecting heparin in a sample, to a diagnostic kit for detecting heparin and to certain uses of the perylene diimide derivatives of formulae I, II and III.

BACKGROUND OF THE INVENTION

Heparin is a naturally occurring polyanionic polysaccharide, consisting of alternating uronic acids and glucosamines. Dependent on the length of the saccharide chain, heparin occurs with molecular weights of 6.000 to 30.000 g/mol. It is naturally produced in mast cells and basophile granulocytes to function as the bodies own coagulants. Most importantly, Heparin reduces blood clotting by activating antithrombin, inhibiting blood clotting factors such as Xa and IIa and by inhibiting thrombocyte aggregation.

Pharmacologically, heparin is used for preventing thrombosis or embolism in the course of surgeries, for reducing thrombotic or embolic reactions associated with extracorporeal cardiovascular systems and for treating acute phase heart insufficiency. Due to the high molecular weight and the anionic properties, heparin must be applied intravenously or subcutaneously. Heparin acts immediately upon administration, but, because it is digested rapidly within the organism, its effect lasts only for a few hours.

As a pharmaceutical, heparin is provided as unfractionated heparin and as low molecular weight heparin (LMWH). The unfractionated heparin is obtained from animal intestine mucosa or lung and mostly contains long chain molecules which are digested rapidly. Moreover, only 30% of the unfractionated heparin is pharmaceutically effective. LMWH, in contrast, is obtained by restricted digestion of native heparin, it is digested slower within the organism and contains a higher fraction of pharmacologically effective molecules. However, it cannot be antagonized by administration of antidotes such as protamine sulfate, bearing the risk of bleedings resulting from over dosage. Thus, to maintain constant heparin levels of unfractionated or low molecular weight heparin, within the body, that are sufficiently inhibiting blood clotting without causing bleedings or other adverse reactions, such as heparin induced thrombocytopenia, regular monitoring of the concentration of heparin in the blood is required.

Commonly, indirect methods as e.g. the prothrombin time method or the factor Xa activity test are used to determine blood clotting conditions. However, these methods do not detect heparin itself and can be influenced by factors other than heparin (Despotis et al., 1999). Some of the established test systems, as e.g. the prothrombin time method are applicable to unfractionated heparin only. Moreover, these methods are time consuming and require laboratory equipment. Thus they are particularly unsuited for emergency medical aid or point-of-care applications. Similar, also electrochemical methods, such as polymer membrane based ion-selective electrodes or ion-selective field effect transistors are elaborate and susceptible to influences of molecules other than heparin.

Recently, methods have been developed, e.g optical tests that rely on color reactions, to detect heparin. The chemical dyes, that have been found to interact with heparin so far, show emission at wavelengths within or close to the blood owns fluorescent and in addition their emission responses are greatly reduced in the presence of blood serum or plasma (Wright et al., 2005; Wang et al., 2008). These side effects may result from strong interference of the serum/plasma matrix with the chemical dyes, leading to a competitive binding of the dye to heparin or matrix molecules. The resulting low signal to background ratio hinders the accurate detection of heparin in blood or blood derived samples. Therefore a fast and easy method to detect heparin is required that also shows a low susceptibility to interfere with matrix molecules of blood, to assure the assays reliability.

SUMMARY OF THE INVENTION

In a first aspect, the present invention relates to a perylene diimide derivative of formula I

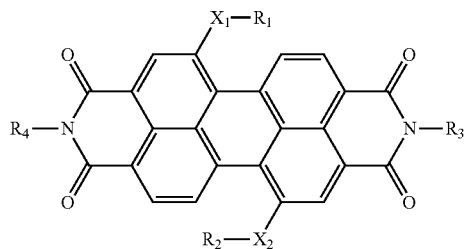

wherein X1 and X2, are the same or different and are selected from the group consisting of S and O, R1 and R2 are the same or different and are $((CA_2)_m\text{-}NA_2)_n$, R3 and R4 are the same or different and are $((CA_2)_o\text{-}NA)_p\text{-}((CA_2)_q\text{-}NA)_r\text{-}(CA_2)_s\text{-}NA_2$, A is selected from the group consisting of H and $CH_3$, and m, n, o, p, q, r, and s are the same or different, preferably 1 to 10, more preferred 1 to 5.

In a further aspect the present invention relates to the perylene diimide derivative of formula II

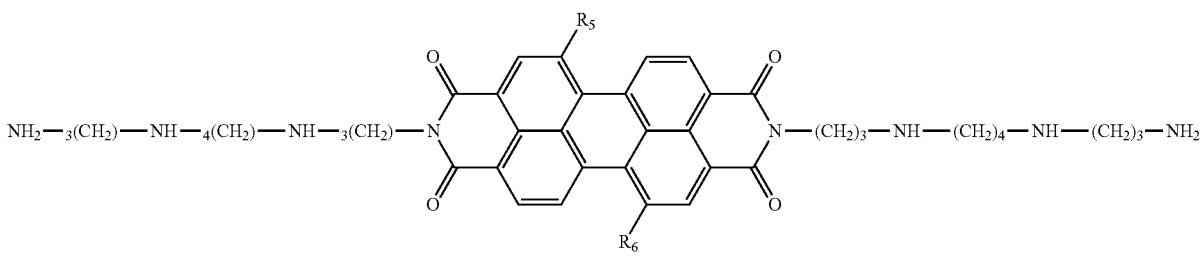

wherein R5 and R6 are the same or different and are selected from the group consisting of S—(CH$_2$)$_2$—NH$_2$ and O—(CH$_2$)$_3$—NH$_2$.

A further aspect of the present invention relates to an in vitro method for detecting heparin in a sample, comprising providing a solution comprising a perylene diimide derivative, adding the sample to be tested for its heparin content to the solution to provide a mixture, measuring a fluorescent signal of the mixture, and comparing the fluorescent signal of the mixture to the fluorescent signal of the solution, wherein an interaction of the perylene diimide derivative with heparin modulates the intensity of the fluorescent signal of the mixture, compared to the solution.

A further aspect of the present invention relates to a method for preparing a perylene diimide derivative of formula I, comprising the steps of converting perylene 3,4,9,10-tetracarboxylic acid dianhydrid to its 1,7 di-bromo derivative, reacting the 1,7 di-bromo derivative with tris-Boc protected amine residues, replacing bromo by nucleophilic amine residues, and de-protecting the amine residues with hydrochloric acid.

In a preferred aspect, the nucleophilic amine residues are selected from the group consisting of S—(CH$_2$)$_2$—NH$_2$ and O—(CH$_2$)$_3$—NH$_2$, and the amine residues are ((CH$_2$)$_3$—NH)—((CH$_2$)$_4$—NH)—(CH$_2$)$_3$—NH$_2$.

A further aspect of the present invention relates to a diagnostic kit for detecting heparin in a sample in vitro, comprising a perylene diimide derivative.

A further aspect of the invention relates to the use of a perylene diimide derivative for detecting heparin in a sample in vitro, preferably for determining the concentration of heparin.

A further aspect of the present invention relates to the use of a perylene diimide derivative for monitoring heparin levels of a patient in vitro, for manufacturing a diagnostic kit for detecting heparin in a sample, for preparing blood preservations, and/or for controlling the quality of heparin by detecting contaminations.

In a further aspect, the present invention relates to the use of a perylene diimide derivative for neutralizing the anticoagulant activity of heparin.

In a further aspect, the present invention relates to the use of a perylene diimide derivative for manufacturing a pharmaceutical composition for antagonizing heparin.

The invention will be more apparent from the disclosure of the following description together with the figures.

DETAILED DESCRIPTION OF THE INVENTION

Figure 1:
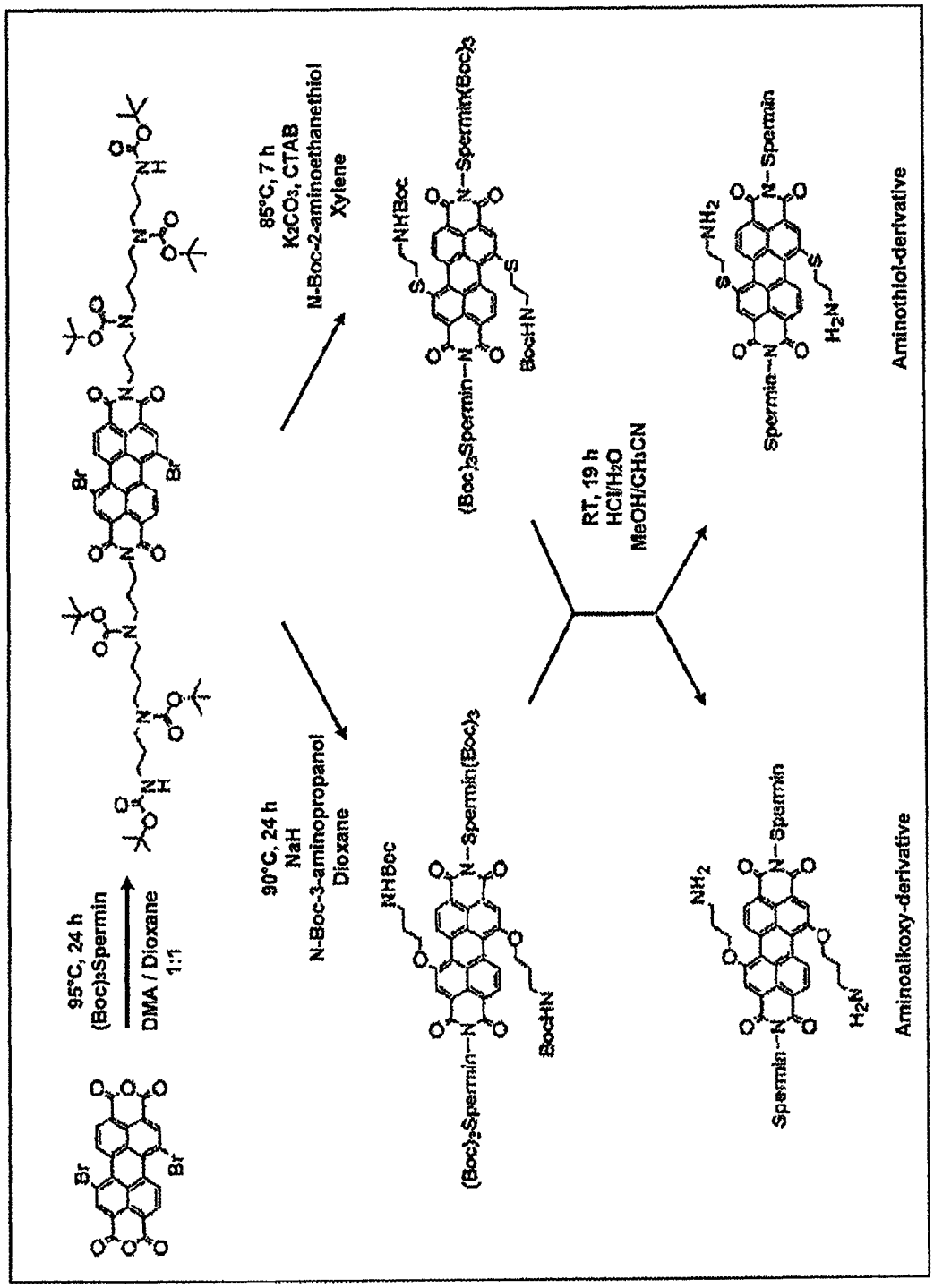
FIG. 1 shows the schematic illustration of the preparation of perylene diimide derivatives (aminoalkoxy- and aminothiol-derivative) from a common precursor molecule.

In a first aspect the present invention relates to a perylene diimide derivative of formula I

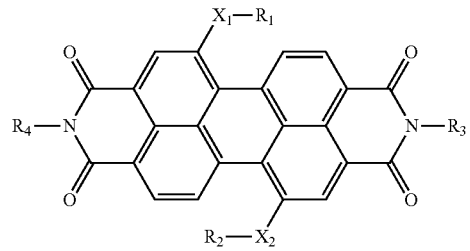

wherein X1 and X2, are the same or different and are selected from the group consisting of S and O, R1 and R2 are the same or different and are ((CA$_2$)$_m$-NA$_2$)$_n$, R3 and R4 are the same or different and are ((CA$_2$)$_o$-NA)$_p$-((CA$_2$)$_q$-NA)$_r$-(CA$_2$)$_s$-NA$_2$, A is selected from the group consisting of H and CH$_3$, and m, n, o, p, q, r, and s are the same or different, preferably 1 to 10, more preferred 1 to 5.

The perylene diimide derivative of the invention is strongly fluorescent due to a high molar absorbidity and good quantum yields. The perylene diimide derivative comprises substitutions at the positions C2 and C6 (bay positions) linked to the perylene diimide derivative by an element selected from the group consisting of oxigen and sulphur. The substitutions at the positions C2 and C6 and the element linking them, influence the photophysical properties of the perylene diimide derivative and shift its fluorescence to longer wavelengths. The strong fluorescence of the perylene diimide derivative is in accordance with its reduced tendency to form nonfluorescent aggregates, due to good solubilisation and electrostatic repulsion. The substitutions binding to the nitrogens of the perylene diimide derivative comprise several, at least 3 amine groups which mediate the interaction with heparin. Upon interaction of the amino groups with heparin, the photophysical properties of the perylene diimide derivative are modulated.

In a preferred embodiment, the perylene diimide derivative is in the form of its ammonium salt, preferably its ammonium chloride salt, more preferred its quaternary ammonium salt obtained by methylation of tertiary ammonium groups. The positive charges of the salt support the binding of the perylene diimide derivative to heparin.

In a preferred embodiment, R3 and R4 are (CH$_2$)$_3$—NH—(CH$_2$)$_4$—NH—(CH$_2$)$_3$—NH$_2$.

In a second aspect the invention relates to the perylene diimide derivative of formula II

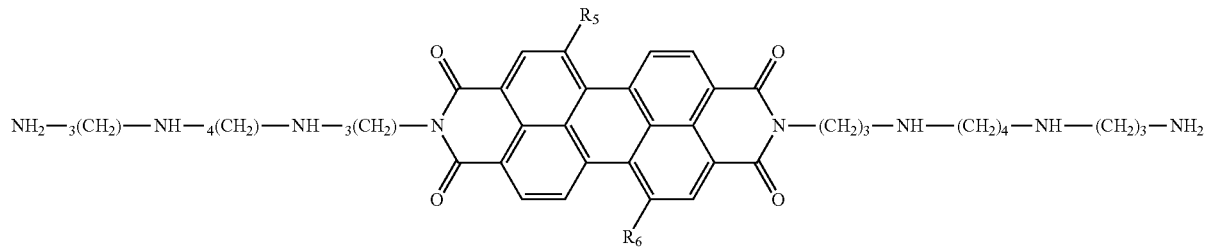

wherein R5 and R6 are the same or different and are selected from the group consisting of S—(CH$_2$)$_2$—NH$_2$ and O—(CH$_2$)$_3$—NH$_2$.

In a third aspect, the invention relates to an isomer to formula II, having the structure of formula III

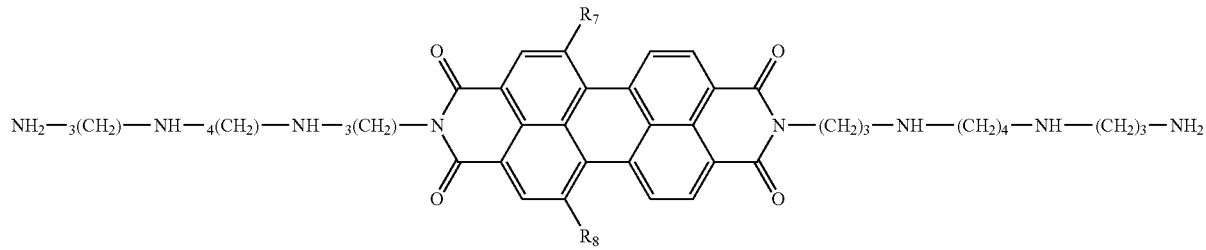

wherein R7 and R8 are the same or different and are selected from the group consisting of S—(CH$_2$)$_2$—NH$_2$ and O—(CH$_2$)$_3$—NH$_2$. This isomer differs from the perylene diimide derivative of formula II with respect to the position (1,7 or 1,6) of the substitutions R7 and R8, but shows similar fluorescence emission responses to heparin in blood serum or blood plasma samples.

In a fourth aspect, the invention relates to a composition of perylene diimide derivatives, comprising a perylene diimide derivative of formula II and a perylene diimide derivative of formula III, wherein R5, R6, R7 and R8 are the same or different and are selected from the group consisting of S—(CH$_2$)$_2$—NH$_2$ and O—(CH$_2$)$_3$—NH$_2$. The perylene diimide derivatives of formula II and III may evolve during the same production process and can be isolated as a 2:1 mixture. However, since both isomers share similar fluorescence properties and binding affinities to heparin, they do not have to be isolated from each other, reducing costs of purification.

In a fifth aspect, the invention concerns an in vitro method for detecting heparin in a sample, comprising the steps of
  a) providing a solution comprising a perylene diimide derivative,
  b) adding the sample to be tested for its heparin content to the solution to provide a mixture,
  c) measuring a fluorescent signal of the mixture, and
  d) comparing the fluorescent signal of the mixture to the fluorescent signal of the solution,
wherein an interaction of the perylene diimide derivative with heparin modulates the intensity of the fluorescent signal of the mixture, compared to the solution.

The term "heparin" as used herein, refers to polyanionic polysaccharides, consisting of alternating uronic acids and glucosamines, with molecular weights of 6.000 to 30.000 g/mol. These polysaccharides are naturally occurring and artificially obtained disaccharide derivatives, such as glucosamine-N-sulfate-, glucosamine-O-sulfate-, glucuronacid-O-sulfate mucopolysaccharides or repeating disaccharides exhibiting properties related to those of heparin. Further comprised is natural, unfractionated heparin, artificial heparin as well as processed heparin as e.g. low molecular weight heparin (LMWH), which has a lower molecular weight than unfractionated heparin, naturally occurring and half or fully synthesized heparinoids and mucopolysaccharides that act similar to heparin, e.g. synthesized pentasaccharide such as fondaparinux and idraparinux. Heparinoids are commonly used as anticoagulants for patients showing intolerance for native heparin or suffering from heparin induced thrombocytopenia.

The term "fluorescent signal" as used herein, refers to a luminescence phenomenon in which an electron de-excitation occurs almost spontaneously, and in which emission from the luminescent substance ceases when the exciting source is removed. The electrons of the fluorescent molecule or moiety absorb a quantum of energy carried by a photon, enter an excited state and emit the energy as a photon of a larger wavelength and of reduced energy. The difference in wavelengths is called the stokes shift and the time taken to emit the photon is called a lifetime ($\tau$). The quantum yield ($\Phi$=number of photons emitted/number of photons excited) indicates the efficiency of the fluorescence molecule or moiety.

The term "interaction" as used herein, refers to any chemical binding between two atoms or molecules, comprising ionic bonding, electrovalence, covalent bonding, van der Waals bonding, metallic bonding, electrostatic interactions and hydrogen bonds. Further comprised are chemical reactions between two or more molecules, repulsion and attraction of molecules, and the exchange of kinetic energy between the same or different molecules.

In a preferred embodiment, the perylene diimide derivative is water soluble, such that the solution can be directly mixed with aqueous samples.

In a preferred embodiment, the perylene diimide derivative has an emission maximum at a wavelength above the background fluorescence of blood, preferably above 550 nm, more preferred above 600 nm. Such an emission maximum is particularly advantageous because it increases the signal to background ratio, thereby improving the detection of the perylene diimide derivative in samples of blood or blood derivatives.

The term "background fluorescence" as used herein, refers to a compounds, compositions or samples own fluorescence, i.e. autofluorescence or primary fluorescence. Blood, for example, and samples derived from blood, show an autofluorescence upon excitation at 480 nm at wavelengths in the range of 480-560 nm. At longer wavelengths the bloods autofluorescence is reduced e.g. by 25%, 11%, and 3% at 620 nm, 650 nm and 700 nm, respectively.

In a preferred embodiment, the perylene diimide derivative comprises at least 3, preferably at least 6, more preferred at least 8 amino groups. The multiple ammonium groups strengthen the electrostatic interaction between the perylene diimide derivative and heparin.

In a particularly preferred embodiment, at least 30%, preferably at least 50% of the amino groups of the perylene diimide derivative are protonated. When isolated in the form of its ammonium salt ($H_8$-perylene diimide derivative)$Cl_8$ at a pH 7.0, at least 6 of the 8 amino groups of the perylene diimide derivative are protonated. In their protonated state, the amino groups function as donors of protons for the negatively charged heparin, thereby strengthening the interaction between both, by inducing hydrogen bonds.

In a preferred embodiment, the perylene diimide derivative has the formula I, II or III.

In a preferred embodiment, the solution comprises a mixture of perylene diimide derivative isomers, avoiding cost intensive isolation processes.

In a preferred embodiment, the solution comprises a mixture of the perylene diimide derivatives of formulae II and III. As both perylene diimide derivative share common photophysical properties and heparin binding characteristics, the molecules can be used in mixture and do not have to be isolated.

In a preferred embodiment, the perylene diimide derivative has a concentration of 0.1 µM to 100 µM. The sensitivity of the method for detecting heparin can be adjusted to the heparin concentration expected to be contained in the sample, by modulating the concentration of the perylene diimide derivative in the solution. Solutions comprising the perylene diimide derivative in low concentrations are particularly useful to accurately measure low concentrations of heparin, e.g. as used during cardiovascular surgery.

In a preferred embodiment, the solution further comprises sodium dodecyl sulfate (SDS), anionic hydrotropes and/or a fluorescence quencher. The sensitivity of the method for detecting heparin can be improved by adding further components to the solution comprising the perylene diimide derivative. The addition of SDS increases the intensity of the fluorescent signal of the perylene diimide derivative, permitting a more accurate detection of low concentrations of heparin. The presence of anionic hydrotropes in the solution comprising the perylene diimide derivative increases both the fluorescent signal and the selectivity of the perylene diimide derivative for heparin compared to other glycosaminoglycans. This reduces the influence of molecules other than heparin, e.g. matrix molecules, on the result of the method, thereby improving its precision. This allows an accurate and reliable detection of heparins even in the presence of other glycosaminoglycans, superseding the processing of blood samples. These advantages privilege the method according to the invention for a point-of-care detection of heparin.

The term "fluorescence quencher" as used herein, refers to polyanionic compounds, which are themselves fluorescent or highly coloured, and form a weakly or non fluorescent complex with the perylene diimide derivative. Such polyanionic compounds are polycarboxylaters or polysulphates which associate with the perylene diimide derivative. Examples include porphyrin derivatives such as tetraphenyl-porphin-4, 4',4'',4'''-tetrasulfonic acid tetrasodium salt (TPPS), and anionic perylene diimide derivatives.

TPPS, for example, shows very intense 405 nm absorbance and 650 nm fluorescence which are abolished when the porphyrin associates with the perylene diimide derivatives. When heparin is added to the mixture of the porphyrin and the perylene diimide derivative, the later binds to heparin and the former is released. Consequently, both, absorbance and fluorescence of the porphyrin, are restored, allowing the quantification of heparin by measuring either 405 nm absorbance or 650 nm fluorescence. The 405 nm absorbance of the porphyrin can be monitored using common photometric devices, usually available in medical facilities. Therefore the method according to the invention provides a fast and reliable detection of heparin which can be applied in most facilities immediately, without further financial investments.

In a preferred embodiment, the sample is selected from the group consisting of whole blood, blood plasma, blood serum and aqueous solutions. The method for detecting heparin is also suited for the analysis of blood preservations, processed blood and other biological matrices. Aqueous solutions are e.g. used for titration methods or medical compositions used e.g. in haemodialysis, haemofiltration, haemoperfusion, surgery, and/or treatments requiring heparinization.

In a preferred embodiment, the interaction of the perylene diimide derivative with heparin is reversible, preferably a reversible chemical bond. Due to the reversibility of the interaction between the perylene diimide derivative and heparin, the addition of other molecules interacting with the perylene diimide derivative or heparin in a competitive manner can be used to restore the fluorescence of the perylene diimide derivative, providing useful applications for control tests and samples.

In a preferred embodiment the interaction of the perylene diimide derivative with heparin reduces the intensity of the fluorescent signal of the mixture compared to the solution. The interaction with heparin changes the photophysical properties of the perylene diimide derivative such that the fluorescent intensity of the perylene diimide derivative is reduced or abolished.

In a particularly preferred embodiment, the reduction of the intensity of the fluorescent signal is linear to the concentration of heparin in the sample. Therefore, in a preferred embodiment the method according to the invention is suited to determine the concentration of heparin in a sample. The linear dependence of the fluorescence simplifies the determination of the concentration of heparin, since an simultaneous analysis of standardized samples is not required.

In a preferred embodiment, the fluorescence signal is detected by measuring emission with a fluorometric device, preferably a portable fluorometer, equipped with a suitable emission and absorbance filter device. The fluorescent signal of the perylene diimide derivative, the solution containing the perylene diimide derivative, the sample and/or the mixture, can be detected using fluorometric devices such as spectrofluorometer, micro plate spectrofluorometer, filterfluorometer, preferably portable fluorometer, fluorometric devices and point-of-care devices on fluorescence detection.

In a preferred embodiment, the method for detecting heparin further comprises the step of generating a titration standard e.g. by determining the reduction of the intensity of the fluorescence signal of the solution upon adding distinct concentrations of heparin. A titration standard permits an immediate quantitative determination of the heparin concentration e.g. in a blood sample.

In a particularly preferred embodiment, the concentration of heparin in the sample is determined by further comparing the fluorescent signal of the mixture to the titration standard. A direct comparison to a titration standard provides a fast and easy way to obtain an accurate result about the concentration of heparin, particularly advantageous for emergency medicine or point-of-care diagnostics.

In a sixth aspect the invention relates to a method for preparing a perylene diimide derivative of formula I, comprising the steps of
  a) converting perylene-3,4,9,10-tetra-carboxylic acid dianhydride to its 1,7 di-bromo derivative,
  b) reacting the 1,7 di-bromo derivative with tris-Boc protected amine residues,
  c) replacing bromo by nucleophilic amine residues, and
  d) de-protecting the amine residues with hydrochloric acid.

A commercially available perylene-3,4,9,10-tetracarboxylic acid dianhydride is converted to its 1,7-dibromo derivative and reacted with tris-Boc protected spermine. The nucleophilic amine residues are added to the bis-spermidine diimide by nucleophilic aromatic substitution reactions, replacing the bromo moieties. These reactions are followed by a de-protection with hydrochloric acid, removing the tris-Boc moieties and recovering the reactive residues of the molecule. By this method, molecules can be generated from available precursors showing distinct photophysical properties and, due to the spermine residues a characteristic interaction with heparin.

In a particularly preferred embodiment, the nucleophilic amine residues are O—R or S—R, wherein R is either a monoamine or a polyamine. These residues lead to a shift of the excitation and emission maxima of the perylene diimide derivative to particularly long fluorescence wavelengths.

In a preferred embodiment, the nucleophilic amine residues are selected from the group consisting of S—$(CH_2)_2$—$NH_2$ and O—$(CH_2)_3$—$NH_2$, and the amine residues are $((CH_2)_3$—NH)—$((CH_2)_4$—NH)—$(CH_2)_3$—$NH_2$. These particular residues cause an emission maximum of the perylene diimide derivative of 625 nm and 570 nm, respectively.

In a seventh aspect the invention relates to a diagnostic kit for detecting heparin in a sample in vitro comprising a perylene diimide derivative. Thus, the invention provides fast and easy means for testing samples for heparin.

In a preferred embodiment, the kit further comprises SDS, anionic hydrotropes, a fluorescence quencher and/or a titration standard, thereby providing means for point-of-care detection e.g. during haemodialysis or haemofiltration.

In a preferred embodiment, the kit further comprises a portable fluorometer or photometer, such that laboratory equipment is not essentially required and an immediate readout is provided, especially for emergency medicine aid and constant heparin monitoring e.g. during surgeries that require complete anticoagulation.

In an eighth aspect the invention relates to the use of a perylene diimide derivative for detecting heparin in a sample in vitro, preferably for determining the concentration of heparin. By the use of the perylene diimide derivative of the invention, heparin can be detected or its concentration can be determined in a fast and direct way. This is particularly important when assessing e.g the coagulation state of a patient during medication or surgery.

In a ninth aspect the invention relates to the use of a perylene diimide derivative for monitoring heparin levels of a patient in vitro. Since heparin acts fast, but is degraded rapidly in the organism, a constant monitoring of the heparin levels in the blood of a patient, provided by an immediate readout, is required for medical care. Such monitoring is needed e.g. during the application of extracorporeal cardiovascular systems, haemodialysis and/or haemofiltration, and it is particularly important for treatments or surgeries requiring complete anticoagulation or for patients suffering from diseases such as kidney insufficiency.

Therefore, in a preferred embodiment, the heparin levels are monitored before, during and/or after medical treatment and/or surgery.

In a particularly preferred embodiment the treatment is selected from a group consisting of extracorporeal cardiovascular system, heamodialysis, haemofiltration, interventional cardiology and intensive care units. These treatments need high to absolute anticoagulation of the patient's blood. However, an uncontrolled reduction of the coagulation properties of the blood bare the risk of undesired and dangerous bleedings. Therefore these treatments are a particularly important field of application of the perylene diimide derivative of the invention.

In a tenth aspect the invention provides the use of a perylene diimide derivative for manufacturing a diagnostic kit for detecting heparin in a sample.

In an eleventh aspect the invention provides the use of a perylene diimide derivative for preparing blood preservation, since this requires the addition of anticoagulants for preservation.

In a twelfth aspect the invention relates to the use of a perylene diimide derivative for controlling the quality of heparin by detecting contaminations of e.g. a heparin comprising composition with other glycosaminoglycanes such as chondroitin sulfate and/or oversulfated chondroitin sulfate (OSCS). Such glycosaminoglycanes are contained in particularly high concentrations in unfractionated heparin, but do not share their pharmacological effect. OSCS has been identified as the contaminant in tainted heparin samples that lead to more than 100 deaths due to severe adverse reactions in the years 2007/2008. As a consequence of this "heparin crisis", heparin monographs were revised and require tests for OSCS with sophisticated analytical instrumentation. Thus, to estimate the effective fraction of heparin it is thus advantageous to determine the contamination with non-effective molecules.

In a preferred embodiment, a perylene diimide derivative is used for rapid and selective detection and/or quantification of OSCS in a heparin sample in the presence or absence of additional molecules, without the need of high definition instruments. Using the perylene diimide derivative of the invention, the presence and/or amount of OSCS can be measured for example by a portable fluorimeter.

In a further preferred embodiment, a polycationic perylene diimide derivative is combined with a fluorescent polyanionic compound or polyanionic perylene diimide derivative to form a nonfluorescent aggregate. On addition of heparin that contains an OSCS contaminant, OSCS selectively disrupts the aggregate by forming a strong complex with the polycationic perylene diimide derivative, and the fluorescence of the polyanionic perylene diimide derivative is restored.

Heparin samples that contain the contaminant oversulfated chondroitin sulfate (OSCS) or other oversulfated glycosaminoglycans are readily identified by the formation of a microprecipitate on mixing with a perylene diimide derivative. The microprecipitate may be visualized by centrifugation/sedimentation or by a filter spot test.

In a thirteenth aspect the invention relates to the use of a perylene diimide derivative for neutralizing the anticoagulant activity of heparin. This aspect is particularly important since LMWH and most heparinoids cannot be antagonized with common heparin antidotes as e.g. protamine sulfate. The binding of a perylene diimide derivative, particularly in the presence of hydrotropes, neutralizes the anticoagulant activity of synthetic pentasaccharides such as fondaparinux or idraparinux. Therefore, in a particularly preferred embodiment the perylene diimide derivative is used for manufacturing a pharmaceutical composition for antagonizing heparin.

EXAMPLES

Example 1

Synthesis of Perylene Diimide Derivatives

Figure 2:
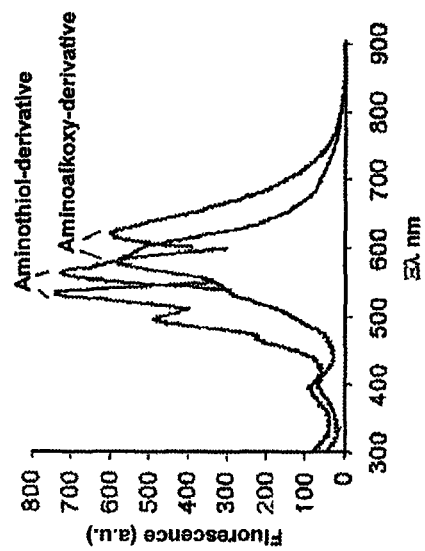
FIG. 2 shows the absorbance and fluorescence emission spectra of the aminoalkoxy-derivative and the aminothiol-derivative.

The inventors generated perylene diimide derivatives to which they attached multiple ammonium groups for strengthening electrostatic probe-target interactions. In addition the inventors introduced O- or S-substitutions at the perylene skeleton. By these substitutions the fluorescence of the perylene diimide derivative was shifted to long wavelengths (red fluorescence). Loss of the fluorescence in aqueous media, due to aggregation, was prevented by attachment of multiple charged substitutions. A new water soluble bis-spermidine diimide of 1,7-dibromo perylene-3,4,9,10-tetracarboxylic acid was prepared by a two-step reaction, starting from commercially available perylene-3,4,9,10-tetracarboxylic acid dianhydride which was converted to the 1,7-dibromo derivative, followed by a reaction with tris-Boc protected spermine. The aminoalkoxy-derivative and aminothiol-derivative were obtained by nucleophilic aromatic substitution reactions of the bis-spermidine diimide with N-Boc protected 3-aminopropanol and 2-aminothioethanol respectively, followed by de-protection with hydrochloric acid. A schematic diagram of the production steps is depicted in FIG. 1. The substitutions at the bay positions had significant influence on the photophysical properties of the perylene diimide derivative. Relative to 1 ($\lambda_{max}$=520 nm), the absorbance maximum of the aminoalkoxy-derivative ($\lambda_{max}$=580 nm) and the aminothiol-derivative ($\lambda_{max}$=530 nm) was red-shifted. The aminoalkoxy- and the aminothiol-derivative were highly fluorescent in buffered water (pH 7.0) with emission maxima at 625 nm and 570 nm, respectively (FIG. 2). The red-shifted fluorescence emission was advantageous for the application to heparin detection in serum because the background fluorescence of blood serum is significantly high at 400-600 nm but strongly decreases above 600 nm.

Perylene diimide derivatives were isolated as a 2:1 mixture of two isomers (perylene diimide derivative of formula II and III) of the same perylene diimide derivative with respect to the position (1,7 or 1,6) of the substitutions. Only the major 1,7-isomers are shown in FIG. 1. Small quantities of the isomers could be isolated by semipreparative HPLC. The perylene diimide derivative of formula III were shown to have similar properties regarding fluorescence emission and heparin interaction as the perylene diimide derivative of formula II. In particular the fluorescence emission response to LMWH in blood serum or blood plasma samples were similar for perylene diimide derivatives of formula II and III, suggesting that both, individually and in combination, are suited to detect heparin.

Example 2

Titration of Perylene Diimide Derivatives

Figure 3:
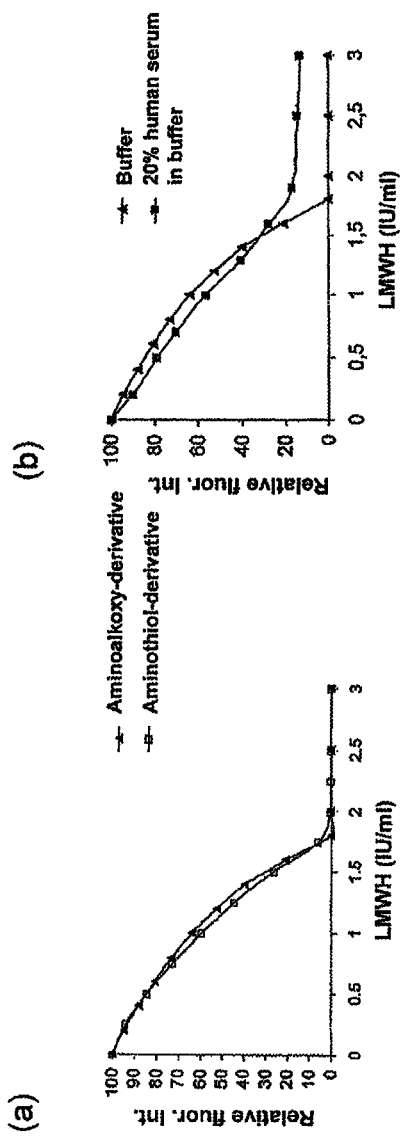
FIG. 3 shows the titration of perylene diimide derivatives with LMWH in buffered solution (a) and in buffered solution containing 20 vol % human serum (aminoalkoxy-derivative) (b).

Heparin cannot be expressed exactly using a conventional chemical formula. Herein, a representative repeating disaccharide (MW=644.2 g/mol) was used as the unit of the molecular weight of heparin, focusing on the detection of LMWH which has a molecular weight of less than 6,000 g/mol. A titration of the aminoalkoxy-derivative and the aminothiol-derivative, respectively, with LMWH was performed in buffered aqueous solution at a pH of 7.0 (10 µM aminoalkoxy-derivative or aminothiol-derivative, 10 mM MOPS, 50 mM NaCl). The perylene diimide derivatives were excited at a wavelength of 485 nm and the fluorescence was measured by detecting the emission fluorescence above 665 nm, using an appropriate filter system. The decrease of fluorescence of a 10 µM solution of the aminoalkoxy-derivative and the aminothiol-derivative, respectively, on titration with heparin is shown in FIG. 3a. The intensity of the fluorescence signal of the perylene diimide derivative decreased above 665 nm with increasing heparin levels. Fluorescence was quenched completely at a sugar to perylene ratio of 3.9. The strongest changes of fluorescence were observed towards the end point of the titration, allowing a very precise quantification.

The same titration was performed with LMWH in buffered aqueous solution (10 mM MOPS, pH 7.0, 50 mM NaCl) containing 20 vol % human serum (FIG. 3b). This revealed a decrease of the intensity of the fluorescence signal of the perylene diimide derivative above 665 nm with increasing heparin levels. Interestingly, a linear decrease of fluorescence with increasing heparin concentrations was observed in the presence of serum. The endpoint of the titration in the presence and absence of serum was observed at about the same heparin concentration, indicating that serum components did not significantly disrupt heparin-perylene diimide derivative interactions. Residual fluorescence at the titration endpoint was attributed to background fluorescence of the serum.

Figure 4:
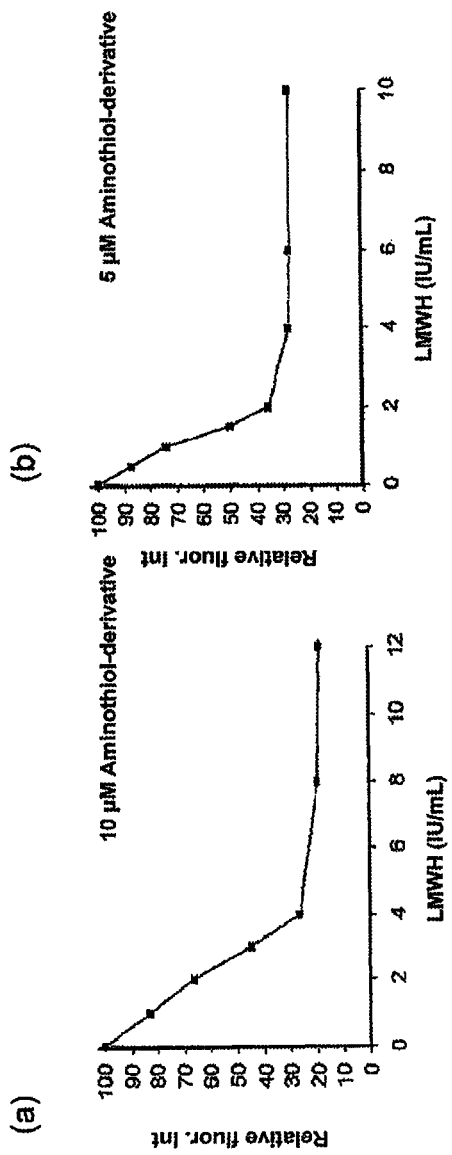
FIG. 4 shows the titration of a perylene diimide derivative (aminothiol-derivative) with LMWH at a concentration of 10 μM (a) and 5 μM (b), and of the aminoalkoxy-derivative in buffer, serum and plasma (c).
Figure 4:
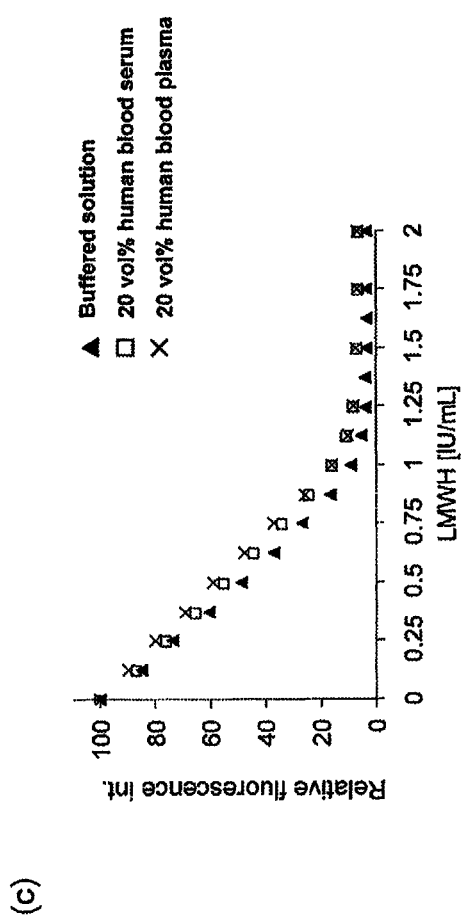

The concentration of the perylene diimide derivative used to detect heparin could be adjusted to optimize detection of low or high concentrations of heparin. In general, heparin is administered at therapeutic dosing levels of 2 to 8 U/mL$^{-1}$ (17 to 67 µM) during cardiovascular surgery and of 0.2 to 1.2 U/mL$^{-1}$ (1.7 to 10 µM) in post-operative and long term care. Responses of the aminothiol-derivative to heparin within the different clinical important ranges are shown in FIGS. 4a and 4b. The fluorescence of a solution comprising the aminothiol-derivative at a concentration of 10 µM (a) or 5 µM (b) in buffered water (pH 7.0), containing 50% human blood serum was measured in the presence of various concentrations of LMWH. The fluorescence emission was measured above 665 nm using an appropriate filter system. At a concentration of 10 µM the fluorescence of the aminothiol-derivative was linearly dependent on heparin concentrations, allowing an accurate readout in the range of 0.5 to 4.0 U/mL heparin (FIG. 4a). A lower concentration range of heparin (0.25 to 2.0 U/mL) was addressed when the aminothiol-derivative was applied in lower concentrations (FIG. 4b).

The response of the perylene diimide derivative to heparin was additionally studied using Dalteparin sodium (0.4-0.8 IU/mL), a clinically important LMWH preparation with a mean molecular weight of 5000 g/mol. Fluorescence was recorded with a portable fluorometer, equipped with a 485 nm excitation filter and a 665 nm cutoff emission filter. The latter filter offered good signal-to-background ratio since serum/plasma autofluorescence is very low above 665 nm. The fluorescence of the perylene diimide derivative decreased approximately linearly (FIG. 4c) with increasing LMWH concentration, in buffered solution. The binding ration was calculated to be one perylene diimide derivative/2 disaccharides of heparin. Solutions containing 20 vol % serum or plasma required an only slightly larger (about 1.1-fold) LMWH concentration to trigger the same relative fluorescence decrease as observed in buffered solution. The response of the perylene diimide derivative to LMWH was fast in all media and binding was reversible since fluorescence was restored on addition of protamine, a strongly heparin-binding polypeptide. Apparently, the perylene diimide derivative associated with LMWH in a highly selective manner, with minimal interference by serum or plasma components.

Example 3

Detection of Heparin Using Additives

Sodium Dodecyl Sulfate (SDS)

Additives were used to significantly improve the fluorescence signal to fluorescence background ratio for heparin detection in serum and plasma samples. The anionic SDS increased the fluorescence of the aminoalkoxy-derivative and the aminothiol-derivative in serum containing samples by a factor of 5 (in the absence of heparin), thus allowing a more accurate quantification of heparin in particular in a lower concentration range.
Fluorescence Quenchers As a representative of "fluorescence quenchers", tetraphenyl-porphin-4,4,4,4-tetrasulfonic acid tetrasodium salt (TPPS) was used to demonstrate the advantageous effect of this type of additives. Association with the perylene diimide derivative (aminoalkoxy-derivative) causes a quenching of both, the 620 nm fluorescence of the perylene diimide derivative and the 650 nm fluorescence of TPPS. In addition, the strong 405 nm absorbance of TPPS (molar absorbance about 500 000 $M^{-1}$ $cm^{-1}$) reduces to <50% of its original value. The sensitivity of the fluoro- and photometric detection of heparin is improved by applying a mixture of both compounds. On addition of heparin, the perylene diimide derivative associates with heparin and TPPS is released. The 405 nm absorbance of TPPS increases linearly with increasing heparin concentration and can be detected by photometric devices. Similarly, the 650 nm fluorescence of TPPS is restored on addition of herparin and can be detected by fluorometric devices. The sensitivity of this modified assay is high enough for accurate detection of heparin at concentrations as low as 0.1 U/ml. An absorbance at a wavelength of 405 nm can be measured by photometric instrumentation widely used for factor Xa assays.
Anionic Hydrotropes Hydrotropes strongly increase the fluorescence of the aminoalkoxy-derivative in serum, in the absence of heparin, without affecting the significant decrease of fluorescence on addition of heparin. Therefore, hydrotropes increase the signal to background ratio and the sensitivity of the heparin detection assay.

Example 4

Detection of Chondroitin Sulfate

The selectivity of the response of a perylene diimide derivative towards heparin in the presence of other glycosaminoglycanes could be enforced by adding hydrotropes.

Figure 5:
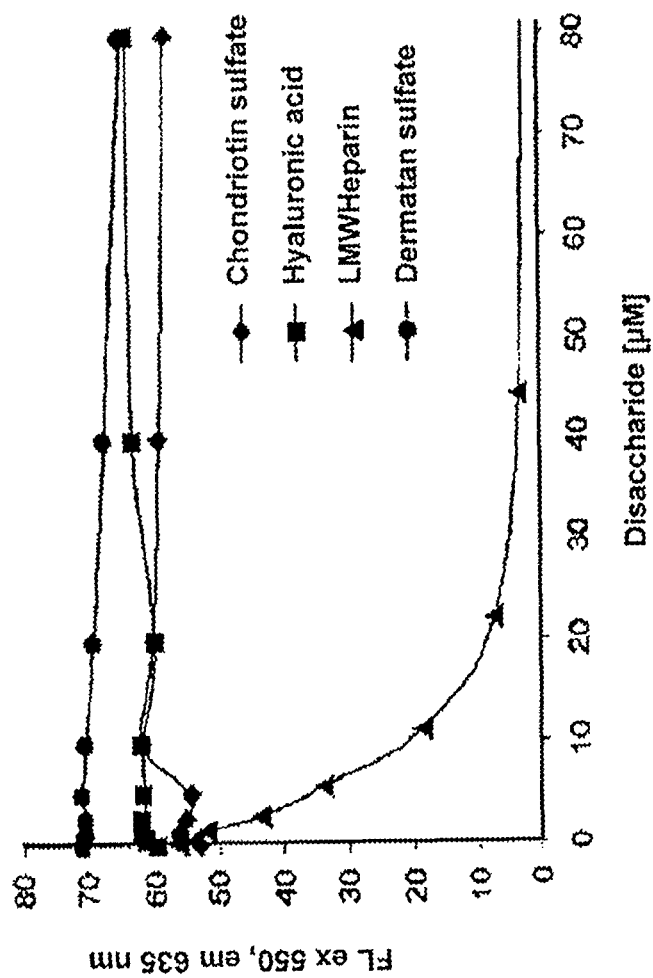
FIG. 5 shows the detection of heparin in buffered solution containing 20 vol % human blood serum in the presence of different glycosaminoglycans.

Changes of fluorescence of the aminoalkoxy-derivative in 20% serum in the presence of a hydrotrope (200 mM) on titration of various glycosaminoglycanes are shown in FIG. 5. The titration of the aminothiol-derivative at a concentration of 1 μM was performed in the presence of different glycosaminoglycans in buffered aqueous solution (60 mM MOPS, pH 7.0, 200 mM pTSNa) containing 25 vol % human blood serum, and the decrease of the intensity of the fluorescence signal above 635 nm was measured. Only LMWH, which has the highest charge to mass ratio, triggered a significant decrease of fluorescence, while the latter remained nearly unchanged for chondroitin sulfate, dermatan sulfate and hyaluronic acid. Traces of chondroitin sulfate impurity in a heparin sample could thus be identified by incubating the aminoalkoxy-derivative with the heparin sample in a buffered solution adding a solution of anionic hydrotropes (100 mM) and measuring the fluorescence emission at 610 nm (excitation at 550 nm). The emission intensity of the solution containing a heparin sample contaminated with chondroitin sulfate or other less sulfonated glycosaminoglycanes was higher compared to the control sample with pure heparin. By this, as little as 5 m/m % of contamination could be detected.

Example 5

Neutralization of Heparin

Figure 6:
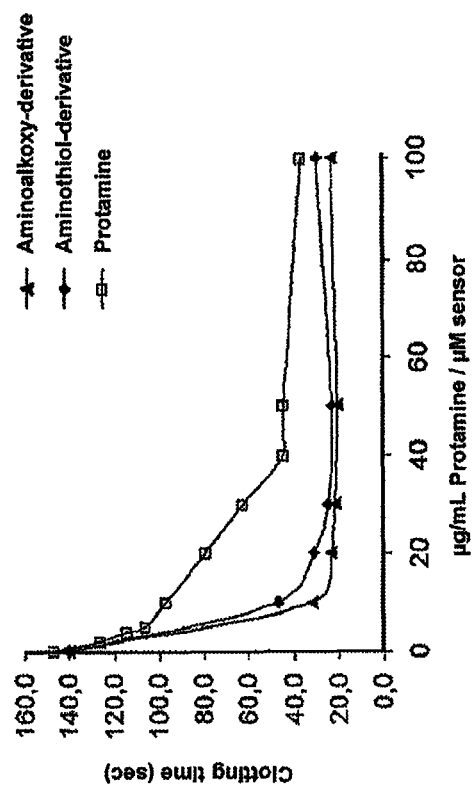
FIG. 6 shows the neutralization of heparin by different perylene diimide derivatives (aminoalkoxy- and aminothiol-derivative), assayed by using the Heptest.

The interaction of perylene diimide derivatives with heparin was also demonstrated using a clotting assay (Heptest). Heparin acts by increasing the clotting time of human plasma by interacting with the plasma proteins. The effect of 1 IU/ml LMWH, however, could be neutralized by the addition of the aminoalkoxy-derivative or the aminothiol-derivative (FIG. 6). This suggested that the interaction of heparin with plasma proteins was disrupted by perylene diimide derivatives. The effect is comparable to that of protamine sulfate, a polyanionic molecule which strongly binds heparin and is therefore used as an antidote.

Figure 7:
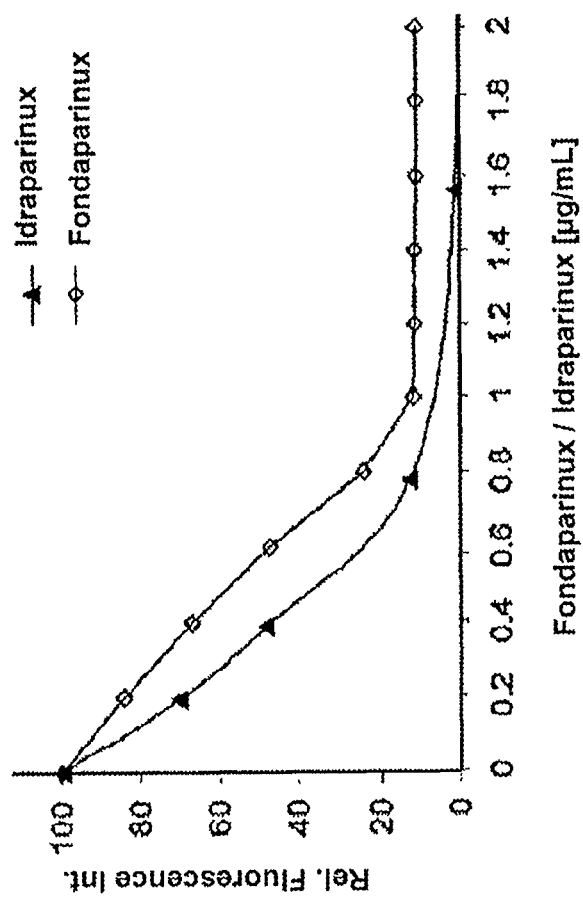
FIG. 7 shows the detection of synthetic pentasaccharides (Idraparinux and Fondaparinux) by perylene diimide derivatives (aminalkoxy-derivative).
Figure 8:
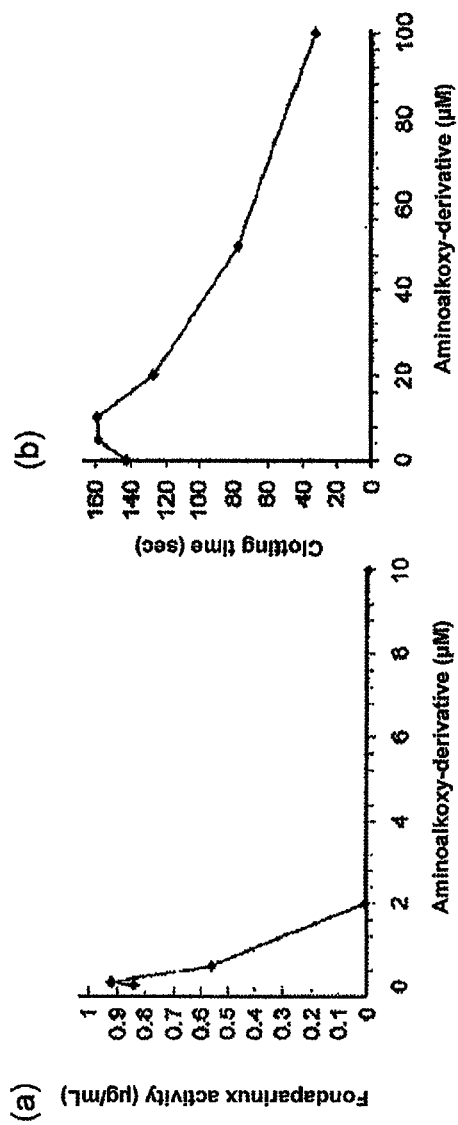
FIG. 8 shows the neutralization of synthetic pentasaccharides by perylene diimide derivatives (aminoalkoxy-derivatives) assayed by using the S-2222 Chromogenic FXa assay (a) and the Heptest assay (b).

As a substitute for heparin, synthetic pentasaccharides as e.g. fondaparinux and idraparinux are used during medical treatment. These synthetic pentasaccharides were detected by the aminoalkoxy-derivative in buffered aqueous solution at pH 7.0. The decrease of intensity of the fluorescent signal of the perylene diimide derivative upon addition of the pentasaccharides is displayed in FIG. 7. The titration of the aminothiol-derivative at a concentration of 1 μM was performed in the presence of different synthetic pentasaccharides in buffered aqueous solution (10 mM MOPS, pH 7.0) and the decrease of the intensity of the fluorescence signal above 635 nm was measured. In addition, low concentrations of the aminoalkoxy-derivative neutralized the anticoagulant activity of fondaparinux, as demonstrated via a chromogenic factor Xa assay (FIG. 8a) and the Heptest (FIG. 8b). The assays were used to determine the neutralization of fondaparinux by the aminoalkoxy-derivative in the presence of 1 μg/ml fondaparinux in human plasma.

Example 6

Analysis of Heparin-Spiked Serum Samples from Patients

Figure 9:
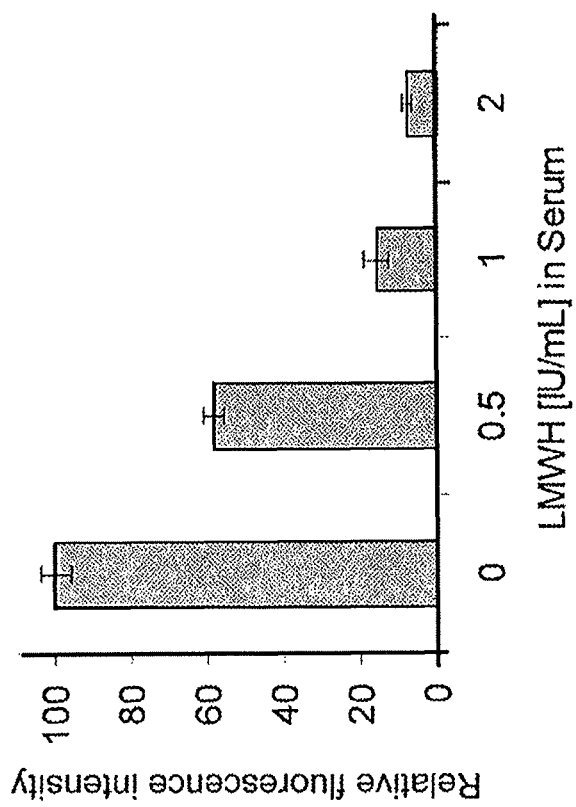
FIG. 9 shows the analysis of heparin in human blood serum samples from five different, heparin-spiked individuals by the aminoalkoxy-derivative.

In an evaluation of inter-individual variations, the inventors analysed the response of the perylene diimide derivatives (aminoalkoxy-derivative) to heparin-spiked serum samples of five randomly selected healthy people. FIG. 9 shows the relative fluorescence of solutions containing the perylene diimide derivative (1 μM), after addition of LMWH-piked (0-2 IU/mL) human blood serum of five different individuals. The fluorescence intensity was measured in heparin-free serum samples and serum samples spiked with 0.5 IU/mL, 1.0 IU/mL LMWH or 2.0 IU/mL. The coefficient of variation CV=(standard deviation)/mean×100 for the five patients at 0.5 IU/mL was 7%. For the validation protocol of anti-Xa assay, the established clinical method for LMWH quantification, the CV even for within-run precision (same sample measured repeatedly) was, depending on instrumentation, in the range 5-18% for comparable heparin levels.

REFERENCES

Despotis, G. J.; Gravlee, G.; Filos, K.; Levy, J.; Anesthesiology 1999, 91, 1122;
Franceschin, M.; Lombardo, C. M.; Pascucci, E.; D'Ambrosio, D.; Micheli, E.; Bianco, A.; Ortaggi, M.; Savino, M.; Bioorg. Med. Chem. 2008, 16, 2292;
Wang, S.; Chang, Y.-T.; Commun. 2008, 10, 1173;
Wright, A. T.; Zhong, Z. L.; Anslyn E. V.; Angew. Chem. Int. Ed. 2005, 44, 5679;

The invention claimed is:

1. A perylene diimide derivative of formula I

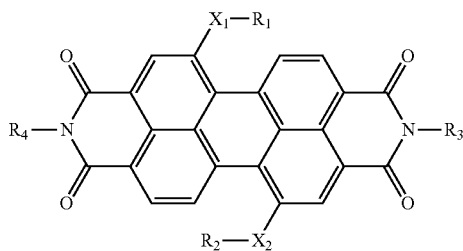

wherein X1 and X2, are the same or different and are selected from the group consisting of S and O;
R1 and R2 are the same or different and are $((CA_2)_m\text{-}NA_2)_n$;
R3 and R4 are the same or different and are $((CA_2)_o\text{-}NA)_p\text{-}((CA_2)_q\text{-}NA)_r(CA_2)_s\text{-}NA_2$;
A is selected from the group consisting of H and $CH_3$, and m, n, o, p, q, r, and s are the same or different wherein m, n, o, p, q, r, and s are each independently 1 to 10.

2. The perylene diimide derivative of claim 1, wherein the perylene diimide derivative is in the form of its ammonium salt, its ammonium chloride salt, or its quaternary ammonium salt.

3. The perylene diimide derivative of claim 1, wherein R3 and R4 are $(CH_2)_3\text{—}NH\text{—}(CH_2)_4\text{—}NH\text{—}(CH_2)_3\text{—}NH_2$.

4. The perylene diimide derivative of claim 1, wherein the perylene diimide derivative is of formula II

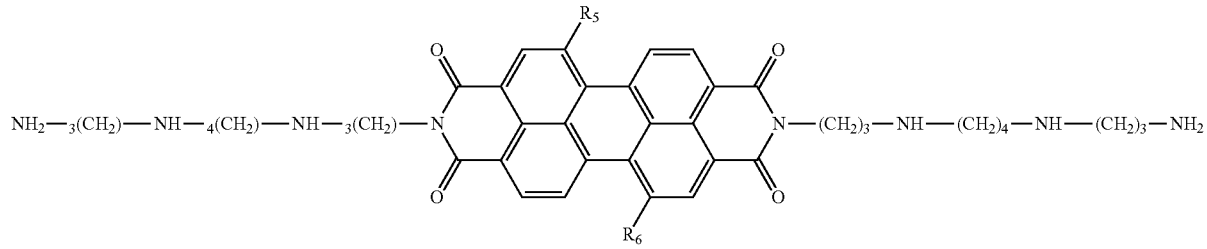

wherein R5 and R6 are the same or different and are selected from the group consisting of $S\text{—}(CH_2)_2\text{—}NH_2$ and $O\text{—}(CH_2)_3\text{—}NH_2$.

5. An in vitro method for detecting heparin in a sample, comprising the steps of a) providing a solution comprising a perylene diimide derivative of formula I according to claim 1,
b) adding the sample to be tested for its heparin content to the solution to provide a mixture,
c) measuring a fluorescent signal of the mixture, and
d) comparing the fluorescent signal of the mixture to the fluorescent signal of the solution, wherein an interaction of the perylene diimide derivative with heparin modulates the intensity of the fluorescent signal of the mixture compared to the solution.

6. The method of claim 5, wherein the perylene diimide derivative has an emission maximum at a wavelength above the background fluorescence of blood, above 550 nm, or above 600 nm.

7. The method of claim 6, wherein the perylene diimide derivative comprises at least 3, at least 6, or at least 8 amino groups.

8. The method of claim 7, wherein at least 30% or at least 50% of the amino groups of the perylene diimide derivative are protonated.

9. The method of claim 5, wherein the solution further comprises sodium dodecyl sulfate, anionic hydrotropes and/or a fluorescence quencher.

10. The method of claim 5, wherein the sample is selected from the group consisting of whole blood, blood plasma, blood serum and aqueous solutions.

11. The method of claim 5, wherein the interaction of the perylene diimide derivative with heparin reduces the intensity of the fluorescent signal of the mixture compared to the solution.

12. A method for preparing a perylene diimide derivative of formula I according to claim 1, comprising the steps of:

a) converting perylene-3,4,9,10-tetra-carboxylic acid dianhydrid to its 1,7 di-bromo derivative,
b) reacting the 1,7 di-bromo derivative with tris-Boc protected amine residues,
c) replacing bromo by nucleophilic amine residues, and
d) de-protecting the amine residues with hydrochloric acid.

13. The method of claim 12, wherein the nucleophilic amine residues are selected from the group consisting of $S\text{—}(CH_2)_2\text{—}NH_2$ and $O\text{—}(CH_2)_3\text{—}NH_2$, and the amine residues are $((CH_2)_3\text{—}NH)\text{—}((CH_2)_4\text{—}NH)\text{—}(CH_2)_3\text{—}NH_2$.

14. A diagnostic kit for detecting heparin in a sample in vitro, comprising a perylene diimide derivative according to claim 1.

15. A method of neutralizing the anticoagulant activity of heparin which comprises using a perylene diimide deriviative according to claim 1.

16. The perylene diimide derivative of claim 1, wherein m, n, o, p, q, r, and s are each independently 1 to 5.

* * * * *